United States Patent
Ito et al.

(10) Patent No.: US 10,441,821 B2
(45) Date of Patent: Oct. 15, 2019

(54) FIRST AGENT FOR HAIR MODIFICATION AND HAIR MODIFICATION TREATMENT METHOD

(71) Applicant: MILBON COMPANY LTD, Osaka-shi, Osaka (JP)

(72) Inventors: Len Ito, Osaka (JP); Yoshihide Okamoto, Osaka (JP)

(73) Assignee: MILBON CO., LTD., Osaka (JP)

( * ) Notice: Subject to any disclaimer, the term of this patent is extended or adjusted under 35 U.S.C. 154(b) by 263 days.

(21) Appl. No.: 15/235,852

(22) Filed: Aug. 12, 2016

(65) Prior Publication Data

US 2017/0056308 A1 Mar. 2, 2017

(30) Foreign Application Priority Data

Aug. 31, 2015 (JP) .................. 2015-170203

(51) Int. Cl.
| | |
|---|---|
| A61K 8/60 | (2006.01) |
| A61K 8/19 | (2006.01) |
| A61K 8/44 | (2006.01) |
| A61K 8/46 | (2006.01) |
| A45D 7/06 | (2006.01) |
| A61Q 5/04 | (2006.01) |
| A45D 2/00 | (2006.01) |
| A45D 2/38 | (2006.01) |
| A45D 1/28 | (2006.01) |
| A61K 8/34 | (2006.01) |
| A61Q 5/12 | (2006.01) |

(52) U.S. Cl.
CPC .................. *A61Q 5/04* (2013.01); *A45D 1/28* (2013.01); *A45D 2/001* (2013.01); *A45D 2/38* (2013.01); *A45D 7/06* (2013.01); *A61K 8/46* (2013.01); *A61K 8/60* (2013.01)

(58) Field of Classification Search
None
See application file for complete search history.

(56) References Cited

U.S. PATENT DOCUMENTS

| | | | | | |
|---|---|---|---|---|---|
| 4,784,848 | A | * | 11/1988 | Koyama | A61K 8/731 424/70.13 |
| 4,913,900 | A | * | 4/1990 | Kolc | A61K 8/345 132/204 |
| 5,200,175 | A | * | 4/1993 | Tabata | A61K 8/345 424/70.51 |
| 5,415,856 | A | * | 5/1995 | Crews | A61K 8/447 132/202 |
| 6,159,485 | A | * | 12/2000 | Yu | A61K 8/44 424/401 |
| 7,459,150 | B2 | * | 12/2008 | Cannell | A61K 8/60 424/70.1 |
| 2010/0061953 | A1 | * | 3/2010 | Luengo | A61Q 1/10 424/70.13 |
| 2012/0142941 | A1 | * | 6/2012 | Ashida | A23L 33/175 548/535 |
| 2013/0251662 | A1 | * | 9/2013 | Wood | A61K 8/817 424/70.51 |

FOREIGN PATENT DOCUMENTS

| | | | | |
|---|---|---|---|---|
| JP | S59-13708 | | 1/1984 | |
| JP | 06122614 | A * | 5/1994 | |
| JP | H06-287110 | | 10/1994 | |
| JP | 2000004836 | A * | 1/2000 | |
| JP | 2000-281540 | | 10/2000 | |
| JP | 2004-26770 | | 1/2004 | |
| JP | 2004-262798 | | 9/2004 | |
| JP | 2010-285390 | | 12/2010 | |
| JP | 2012-171889 | | 9/2012 | |
| JP | 2016113443 | A * | 6/2016 | |
| WO | WO-2009063042 | A1 * | 5/2009 | ............... A61K 8/46 |
| WO | WO 2015002323 | A1 * | 1/2015 | ............... A61K 8/19 |

OTHER PUBLICATIONS

Wikipedia "Chelation," last modified Apr. 2, 2017; https://en.wikipedia.org/wiki/Chelation.*
Sears "Chelation: Harnessing and Enhancing Heavy Metal Detoxification—A review," Scientific World Journal 2013:1-13, 2013.*
Machine translation, JP 2000-004836, printed 2017.*
CAS "Ammonium bicarbonate," printed 2017.*
CAS "Ammonium dithioglycolate," printed 2017.*
Wikipedia "Trehalose," last edited Jun. 26, 2018; https://en.wikipedia.org/wiki/Trehalose.*
PubChem "N-actylglucosannine," printed 2018.*
Wikipedia "N-acetylglucosamine," last edited Jun. 27, 2018.*

* cited by examiner

*Primary Examiner* — Bethany P Barham
*Assistant Examiner* — Dominic Lazaro
(74) *Attorney, Agent, or Firm* — Morrison & Foerster LLP

(57) ABSTRACT

The first agent for hair modification is appliable on hair in a reduction step for a hair modification treatment method including a reduction step; and a heating step of bringing the hair obtainable after the reduction step into contact with a heating element set at a temperature of 70° C. or higher, the first agent including a reducing agent and N-acetylglucosamine. The hair modification treatment method includes a reduction step of applying, on hair, a first agent for hair modification including a reducing agent and N-acetylglucosamine; and a heating step of bringing the hair obtainable after the reduction step into contact with a heating element set at a temperature of 70° C. or higher.

5 Claims, No Drawings

FIRST AGENT FOR HAIR MODIFICATION AND HAIR MODIFICATION TREATMENT METHOD

CROSS-REFERENCE TO RELATED APPLICATION

The present application claims priority benefit of Japanese Patent Application No. JP2015-170203, filed Aug. 31, 2015, and this application, including the specification, claims, drawings, and abstract, is incorporated herein by reference in its entirety for all purposes.

FIELD OF THE INVENTION

The present invention relate to a first agent for hair modification, which is usable in a process for a hair modification treatment including a step of bringing a heating element such as a high temperature curling iron into contact with the hair, and to a hair modification treatment method of using this first agent.

BACKGROUND OF THE INVENTION

In a hair modification treatment of changing the hair shape close to a wave form or a straight form, a first agent for hair modification including a reducing agent is usable, and cleavage of cystine bonds in hair caused by that reducing agent enables modification of the hair shape. Furthermore, in a process for hair modification treatment, there are occasions in which the hair is heated, and there is known a method of heating hair that is coated with a first agent for hair modification to a temperature of 60° C. or lower, for the purpose of promoting the penetration of the first agent for hair modification into the hair. In addition to that, there are also occasions in which the hair is brought into contact with a heating element at a higher temperature, and there is also known a method of washing away the first agent for hair modification from the hair, and then heating the hair with a heating element such as a rod at a temperature of 70° C. or higher, or a hair iron at a temperature of 100° C. or higher.

Heating as described above may intensify the damage of hair, and as the heating temperature is higher, the possibility of hair being damaged is increased. Since the feeling of hair to the touch is deteriorated as the hair is damaged, suggestions have been made to suppress the deterioration. For example, JP 2004-26770 A discloses a hair straightening treatment carried out by using a hair iron, which is a kind of hair modification treatment, and also discloses that gluconic acid and trehalose are incorporated into a first agent for hair straightening so as to promote enhancement of a moist feeling and softness of hair when the hair is subjected to the aforementioned treatment.

SUMMARY OF THE INVENTION

In regard to the feeling of hair that has been subjected to a hair modification treatment involving heating at high temperature, there are occasions in which, as described above, softness is required. There are also occasions in which a smooth feeling at the surface of hair, or a moisturized feeling to the touch is required.

In view of such circumstances, an object of the embodiments of the invention is to provide a first agent for hair modification which imparts an excellent soft feeling to hair when the hair is subjected to a hair modification treatment involving heating at high temperature, and to provide a hair modification treatment method of using the relevant first agent.

The inventors of the present invention conducted a thorough investigation, and as a result, the inventors found that in a case in which a hair modification treatment involving heating at high temperature is performed, when a first agent for hair modification including N-acetylglucosamine is used, the hair acquires an excellent soft feeling, thus completing embodiments of the invention.

That is, a first agent for hair modification according to an embodiment is a first agent for hair modification that can be applied on hair in a reduction step for a hair modification treatment method which includes a reduction step; and a heating step of bringing the hair that has been subjected to the relevant reduction step, into contact with a heating element set at a temperature of 70° C. or higher, and the first agent for hair modification includes a reducing agent and N-acetylglucosamine. When the first agent for hair modification related to the embodiment is used, a satisfactory moisturized feeling of hair is obtainable.

The set temperature of the heating element is, for example, 80° C. or higher and 230° C. or lower.

It is suitable for the first agent for hair modification related to the embodiment that a chelating agent is further incorporated into the first agent. This incorporation of a chelating agent is adequate for enhancing a soft feeling and a smooth feeling of the hair.

It is suitable for the first agent for hair modification related to the embodiment that trehalose is further incorporated into the first agent. This incorporation of trehalose is adequate for enhancing a soft feeling, a smooth feeling, and a moisturized feeling of the hair.

Furthermore, a hair modification treatment method according to another embodiment includes a reduction step of applying, on hair, a first agent for hair modification including a reducing agent and N-acetylglucosamine; and a heating step of bringing the hair that has been subjected to the reduction step, into contact with a heating element set at a temperature of 70° C. or higher.

According to some embodiments, since a first agent for hair modification having N-acetylglucosamine incorporated therein together with a reducing agent can be applied on hair before the hair is brought into contact with a heating element, the hair acquires an excellent soft feeling after the hair modification treatment.

DETAILED DESCRIPTION OF THE INVENTION

The present invention will be explained below based on embodiments of the invention.

The first agent for hair modification (hereinafter, the "first agent for hair modification" may be referred to as "first agent") according to this embodiment is a product in which a reducing agent and N-acetylglucosamine are mixed with water (the mixing amount of water is, for example, 60% by mass or more). Furthermore, in the first agent according to this embodiment, a chelating agent and an alkali agent may also be incorporated, similarly to those known first agents, and the raw materials incorporated into a known first agent may also be incorporated as optional raw materials.

In the first agent according to this embodiment, any one kind or two or more kinds selected from those reducing agents included in known first agents, may be incorporated. The reducing agent may be a known reducing agent having a thiol group, and examples thereof include thioglycolic acid, thioglycolic acid salts (ammonium thioglycolate, thioglycolic acid monoethanolamine, and the like), cysteamine, cysteamine salts (cysteamine hydrochloride, and the like), cysteine (L-cysteine, DL-cysteine, and the like), cysteine salts (L-cysteine hydrochloride, DL-cysteine hydrochloride, and the like), acetylcysteine (N-acetyl-L-cysteine, and the like), glyceryl thioglycolate, thiolactic acid, thiolactic acid salts, and butyrolactone thiol. Examples of other known reducing agents include sulfurous acid salts (sodium sulfite, and the like). In order to impart a satisfactory smooth feeling to the hair surface, thioglycolic acid, a thioglycolic acid salt, cysteine, a cysteine salt, or a sulfurous acid salt may be incorporated into the first agent.

The amount of incorporation of the reducing agent for the first agent in some embodiments may be appropriately set, and for example, the amount of incorporation is from 2% by mass to 15% by mass.

In the first agent in some embodiments, as described above, N-acetylglucosamine is incorporated. As a result of the incorporation of N-acetylglucosamine, the hair acquires an excellent soft feeling. It is considered to be because N-acetylglucosamine suppresses the aggregation of the constituent proteins of hair occurring as a result of the contact with a heating element.

The amount of incorporation of N-acetylglucosamine in the first agent in some embodiments is from 0.001% by mass to 5% by mass in order to obtain sufficient softness of hair, and the amount of incorporation of N-acetylglucosamine is desirably from 0.005% by mass to 2% by mass, and preferably from 0.005% by mass to 1% by mass.

In the first agent in some embodiments, any one kind or two or more kinds selected from those chelating agents incorporated into known first agents may be incorporated. Examples of the chelating agents include edetic acid, edetic acid salts (disodium edetate, trisodium edetate, tetrasodium edetate, dipotassium edetate, and the like), diethylenetriaminepentaacetic acid, diethylenetriaminepentaacetic acid salts (pentasodium diethylenetriaminepentaacetate and the like), ethylenediamine hydroxyethyl triacetic acid, ethylenediamine hydroxyethyl triacetic acid salts (trisodium ethylenediamine hydroxyethyl triacetate and the like), hydroxyethanediphosphonic acid, and hydroxyethanediphosphonic acid salts (tetrasodium hydroxyethanediphosphonate and the like). In regard to the first agent in some embodiments, incorporation of a chelating agent together with N-acetylglucosamine is appropriate for enhancing the soft feeling and smooth feeling of the hair.

The amount of incorporation of the chelating agent in the first agent in some embodiments is, for example, from 0.05% by mass to 2% by mass, desirably from 0.1% by mass to 1% by mass, and preferably from 0.1% by mass to 0.4% by mass. When the amount of incorporation is 0.05% by mass or more, the amount is suitable for obtaining a satisfactory moisturizing feeling of the hair, and when the amount of incorporation is 2% by mass or less, the amount is suitable for obtaining a satisfactory soft feeling of the hair.

In the first agent in some embodiments, one kind or two or more kinds of alkali agents for adjusting the pH to the alkali side are incorporated as necessary. Examples of these alkali agents include ammonia, aminoalcohols (monoethanolamine, triethanolamine, isopropanolamine, 2-amino-2-methyl-1-propanol, 2-amino-2-methyl-1,3-propanediol, and the like), basic amino acids (arginine and the like), morpholine, carbonic acid salts (ammonium carbonate, ammonium hydrogen carbonate, sodium carbonate, sodium hydrogen carbonate, and the like), phosphoric acid salts (ammonium monohydrogen phosphate, sodium monohydrogen phosphate, and the like), and caustic alkalis (potassium hydroxide and sodium hydroxide).

In the first agent in some embodiments, as described above, materials that are appropriately selected from the raw materials for known first agents are optionally incorporated. In the case of incorporating an optional raw material, it is suitable to incorporate trehalose. Other examples of the optional raw materials include a nonionic surfactant, an anionic surfactant, a cationic surfactant, an amphoteric surfactant, a polymeric compound, a silicone, a hydrocarbon, a wax, a higher alcohol, a polyhydric alcohol, a fatty acid, oils and fats, an ester oil, a protein, an amino acid, an anti-inflammatory agent, an antiseptic agent, and a fragrance.

When trehalose is incorporated into the first agent in some embodiments, hair acquires a satisfactory soft feeling, a satisfactory smooth feeling, and a satisfactory moisturizing feeling. The amount of incorporation of trehalose in the first agent in some embodiments is, for example, from 0.1% by mass to 5% by mass, desirably from 0.2% by mass to 2% by mass, and preferably from 0.2% by mass to 1% by mass. When the amount of incorporation is 0.1% by mass, the amount of incorporation is suitable for enhancing the moisturizing feeling of the hair, and when the amount of incorporation is 5% by mass or less, the amount of incorporation is suitable for enhancing the soft feeling of the hair.

In regard to the first agent in some embodiments, the dosage form is not particularly limited as described below; however, the first agent may be prepared into a cream form by incorporating a higher alcohol and a cationic surfactant therein.

The fatty alcohol may be an alcohol having from 14 to 22 carbon atoms, and examples thereof include linear saturated alcohols such as myristyl alcohol, cetyl alcohol, stearyl alcohol, arachidyl alcohol, and behenyl alcohol; linear unsaturated alcohols such as oleyl alcohol; and branched saturated alcohols such as hexyldecanol, octyldodecanol, isocetyl alcohol, and isostearyl alcohol. It is desirable to incorporate one kind or two or more kinds of higher alcohols, and the amount of incorporation of the higher alcohol in the first agent in some embodiments is, for example, from 2% by mass to 6% by mass.

Examples of the cationic surfactant include di-long-chain alkyldimethylammonium salts such as distearyldimethylammonium chloride, dicetyldimethylammonium chloride, and dicocoyldimethylammonium chloride; mono-long-chain alkyltrimethylammonium salts such as behenyltrimethylammonium chloride, behenyltrimethylammonium methosulfate, stearyltrimethylammonium chloride, stearyltrimethylammonium bromide, and cetyltrimethylammonium bromide; and long-chain alkoxyalkyltrimethylammonium salts such as stearoxypropyltrimethylammonium chloride. It is desirable to incorporate one kind or two or more kinds of cationic surfactants, and the amount of incorporation of the cationic surfactant in the first agent in some embodiments is, for example, from 1% by mass to 5% by mass.

The dosage form at the time of use of the first agent in some embodiments is not particularly limited, and examples include a liquid form, a cream form, and a gel form. In order to suppress running down of the first agent that has been applied on the hair, a cream form or a gel form is desirable.

The viscosity of the first agent in some embodiments is not particularly limited. In order to suppress running down from the hair, the viscosity of the first agent is desirably 2,000 mPa·s or more, preferably 4,000 mPa·s or more, more preferably 8,000 mPa·s or more, and even more preferably 10,000 mPa·s or more. Also, in order to increase penetrability of the first agent into the hair, the viscosity of the first agent is desirably 30,000 mPa·s or less, preferably 25,000 mPa·s or less, and more preferably 20,000 mPa·s or less. Meanwhile, for the viscosity in some embodiments, a value measured 60 seconds later at 25° C. using a rotor selected according to the viscosity in a Brookfield viscometer, is employed.

The pH of the first agent in some embodiments may be, for example, from 8.0 to 10.0 at 25° C.

In a hair modification treatment of using the first agent in some embodiments, it is suitable to use a second agent for hair modification (hereinafter, the "second agent for air modification" may be referred to as "second agent") including an oxidizing agent. The second agent in some embodiments may be a known second agent suitable for a hair modification treatment.

The second agent in some embodiments is a product in which an oxidizing agent is mixed with water (a typical second agent in some embodiments has an amount of incorporation of water of 75% by mass or more). Also, in the second agent in some embodiments, those raw materials that are incorporated into known second agents may be incorporated as optional raw materials.

The oxidizing agent that is incorporated into the second agent in some embodiments may be a hydrobromic acid salt (sodium hydrobromide, potassium hydrobromide, or the like) or hydrogen peroxide, as in the case of known second agents.

In the second agent in some embodiments, as described above, those raw materials that are appropriately selected from those known raw materials for the second agent, are optionally incorporated. Examples of these optional raw materials include a nonionic surfactant, an anionic surfactant, a cationic surfactant, an amphoteric surfactant, a polymeric compound, a silicone, a hydrocarbon, a wax, a higher alcohol, a polyhydric alcohol, a fatty acid, oils and fats, an ester oil, a protein, an amino acid, a chelating agent, an anti-inflammatory agent, an antiseptic agent, preservative, and a fragrance.

The dosage form at the time of use of the second agent in some embodiments is not particularly limited, and examples thereof include a liquid form, a cream form, and a foam form (bubble form).

Regarding the pH of the second agent in some embodiments, in a case in which a hydrobromic acid salt is incorporated, the pH is, for example, from 5.0 to 7.5 at 25° C. Furthermore, in a case in which hydrogen peroxide is incorporated, the pH of the second agent in some embodiments is, for example, from 2.5 to 3.5 at 25° C.

The hair modification treatment in some embodiments includes a reduction step of applying the first agent in some embodiments on hair; and a heating step of heating the hair obtainable after the reduction step. Furthermore, in regard to the oxidation of hair obtainable after the heating step, an oxidation step of applying the second agent in some embodiments on the hair results in a higher degree of hair modification, compared to air oxidation by which an agent is not brought into contact.

In the reduction step for the hair modification treatment in some embodiments, the first agent in some embodiments can be applied on the hair, and the hair is left to stand at normal temperature or at or below 60° C. As the standing time at this time is longer, the hair tends to be more easily softened, and for example, the standing time is from 10 minutes to 20 minutes.

In the heating step for the hair modification treatment in some embodiments, after the reduction step, the first agent on the hair is washed away, and the hair is brought into contact with a heating element set at a temperature of 70° C. or higher. The contact may be performed using a known hair iron for straightening hair and making the hair shape close to a straight shape, a rod for making the hair shape into a wavy shape, or a curling iron for making the hair shape into a curled shape or a wavy shape.

Known examples of the hair iron for making the hair shape close to a straight shape include "ADST PREMIUM DS" manufactured by HAKKO, Ltd., and "VSI-1009/PJ" manufactured by Koizumi Seiki Corp. This hair iron includes a pair of metal plate-shaped bodies that face each other as heating elements. When the hair iron is used, as is known, dry hair or almost dried hair is interposed between the facing heating elements, and then while the state of having the hair interposed therebetween, the hair iron is moved so that the interposed hair is smoothened.

The set temperature of the heating elements of the hair iron is 70° C. or higher, desirably 80° C. or higher, preferably 100° C. or higher, more preferably 140° C. or higher, and even more preferably 160° C. or higher, in order to modify the hair shape efficiently. On the other hand, the set temperature of the heating elements is desirably 230° C. or lower, preferably 210° C. or lower, more preferably 200° C. or lower, and even more preferably 190° C. or lower, in order to suppress damage of the hair.

The rod for making the hair shape into a wavy shape is included in known apparatuses, and examples of the apparatuses include "ODIS EX" manufactured by Oohiro Co., Ltd. Wetted hair is wound around the rod, and then the contacting surface of the hair on the rod is increased to a predetermined temperature. It is general to dry the hair by the heat of the rod.

The set temperature of the rod is 70° C. or higher, and desirably 80° C. or higher, in order to modify the shape of the hair efficiently. On the other hand, the upper limit of the set temperature of the rod may be 100° C., which is a temperature for drying the hair.

Known examples of the curling iron for making the hair shape into a curled shape or a wavy shape include "DIGITAL PERMING" manufactured by Hakko, Ltd. This curling iron is used by adjusting the set temperature of the heating element to be, for example, 140° C. or higher and 190° C. or lower.

In the oxidation step for the hair modification treatment in some embodiments, the second agent in some embodiments can be applied on the hair, and the hair is left to stand. The standing time at this time is, for example, from 3 minutes to 15 minutes. After the standing, the hair is desirably washed and dried.

Hereinafter, the embodiments will be described in detail by way of Examples; however, the embodiments are not intended to be limitedly interpreted based on this description of Examples.

Examples 1a and 1b, Examples 2 to 4,
Comparative Examples 1a and 1b, and
Comparative Examples 2 to 4

As the first agents for Examples and Comparative Examples, cream-shaped first agents were produced by mixing raw materials selected from a common component (details will be described below), N-acetylglucosamine, trehalose, ammonium thioglycolate, cysteamine hydrochloride, L-cysteine hydrochloride, anhydrous sodium sulfite, pentasodium diethylenetriamine pentaacetate, ammonium hydrogen carbonate and diammonium dithiodiglycolate, with water at the mixing concentrations described in the following Tables 1 to 4, and adjusting the pH to 9.3 using monoethanolamine.

The common component in the following Tables 1 to 4 is a mixture of raw materials and water, and the raw materials and their mixing concentrations are as follows: dicetyl phosphate 0.2% by mass, polyoxyethylene cetyl ether phosphate 1% by mass, polyoxyethylene cetyl ether 0.5% by mass, stearyltrimethylammonium chloride 2% by mass, cetostearyl alcohol 6% by mass, 1,3-butylene glycol 1% by mass, glycerin 1% by mass, paraffin 0.2% by mass, beeswax 0.2% by mass, soft lanolin fatty acid cholesteryl 0.1% by mass, urea 0.3% by mass, high-polymerized methylpolysiloxane 0.1% by mass, aminoethylaminopropylsiloxane-dimethylsiloxane copolymer 0.1% by mass, and a fragrance 0.1% by mass.

About 2 g of a hair bundle composed of hair strands that were approximately 25 cm long and had a history of being subjected to an oxidative hair dyeing treatment, was washed, and moisture was wiped with a towel. A hair modification treatment including a reduction step, a heating step, and an oxidation step was carried out. In the reduction step, any one of the first agents of Examples and Comparative Examples was applied on the hair bundle, and the hair bundle was passed through a comb and left to stand for about 20 minutes at room temperature. In the heating step, the hair bundle obtainable after the reduction step, which was treated with warm water to wash away the first agent and was dried with warm air blow, was used as an object of treatment. The set temperature of a pair of heating elements in a hair iron ("ADST PREMIUM DS HAIR STRAIGHTENER FOR PROFESSIONAL, ADST PREMIUM DS (FDS-25)" manufactured by Hakko, Ltd.) was set at 180° C., the hair bundle was interposed between the heating elements, and then the hair bundle was slid between the heating elements while being stretched. In the oxidation step, a second agent (the details are described below) was applied on the hair bundle, and the hair bundle was left to stand for about 5 minutes at room temperature. After the standing, the hair bundle was washed with warm water and dried by blowing warm air.

The second agent for the hair modification treatment is a product obtainable by mixing raw materials with water, and the raw materials and the mixing concentrations thereof are as follows: hydrogen peroxide 2% by mass, sodium monohydrogen phosphate 1% by mass, phosphoric acid 0.3% by mass, phenoxyethanol 0.2% by mass, hydroxyethanediphosphonic acid 0.1% by mass, and diethylene glycol monoethyl ether 0.1% by mass. The pH was 3.0.

(Evaluation 1)

Hair bundles were subjected to the hair modification treatment described above, using the first agents of Examples 1a and 1b and Comparative Examples 1a and 1b, and an evaluation based on a comparison between the hair bundles was carried out by five evaluators. Here, the evaluation was carried out by rating the score of a hair bundle having the best feeling to the touch as "4"; the score of a hair bundle having the second best feeling to the touch as "3"; the score of a hair bundle having the third best feeling to the touch as "2"; and the score of a hair bundle having the fourth best feeling to the touch as "1". The average values of the scores were used as an index of the evaluation.

The results of the Evaluation 1 are presented in the following Table 1.

TABLE 1

|  |  | Example 1a | Example 1b | Comparative Example 1a | Comparative Example 1b |
|---|---|---|---|---|---|
|  | Common component | 65 | 65 | 65 | 65 |
|  | N-acetylglucosamine | 0.1 | 0.1 | — | — |
|  | Trehalose | — | 0.9 | — | 0.9 |
| Reducing agent | Ammonium thioglycolate | 3.7 | 3.7 | 3.7 | 3.7 |
|  | Cysteamine hydrochloride | — | — | — | — |
|  | L-cysteine hydrochloride | — | — | — | — |
|  | Anhydrous sodium sulfite | — | — | — | — |
| Chelating agent | Pentasodium diethylenetriamine pentaacetate | 1 | 1 | 1 | 1 |
| Alkali agent | Ammonium hydrogen carbonate | 0.4 | 0.4 | 0.4 | 0.4 |
|  | Diammonium dithiodiglycolate | 2.9 | 2.9 | 2.9 | 2.9 |
| Evaluation 1 | Softness | 2.4 | 4 | 1.6 | 2 |
|  | Smoothness | 2.8 | 3.6 | 1.4 | 2.2 |
|  | Moisturizing feeling | 3 | 3.4 | 1.6 | 2 |

Unit of amount of incorporation: mass %

From a comparison between Example 1a and Comparative Examples 1a and 1b in Table 1, which is related to first agents including ammonium thioglycolate, it was confirmed that all of the feelings of softness, smoothness and a moisturizing feeling became satisfactory as a result of the incorporation of N-acetylglucosamine. Furthermore, it was confirmed from the evaluation results of Example 1b that more satisfactory feelings were obtainable when N-acetylglucosamine and trehalose were incorporated.

(Evaluation 2)

Hair bundles were subjected to the hair modification treatment described above, using the first agents of Examples 2 to 4 and Comparative Examples 2 to 4, and an evaluation based on a comparison between the hair bundles was carried out by four evaluators. The evaluation was performed for each of the following Tables 2 to 4, and a comparison was made between a reference hair bundle defined in each Table and the hair bundles. The significance of these evaluation results were as follows.

◯: Better than the reference (two or more evaluators rated the hair bundle to be better than the reference)

-: Same as the reference (one or fewer evaluators rated the hair bundle to be better than the reference)

x: Poorer than the reference (two or more evaluators rated the hair bundle to be poor)

The results of the Evaluation 2 are presented in the following Tables 2 to 4.

TABLE 2

|  |  | Example 2 | Comparative Example 2 |
|---|---|---|---|
|  | Common component | 65 | 65 |
|  | N-acetylglucosamine | 0.1 | — |
|  | Trehalose | 0.9 | — |
| Reducing agent | Ammonium thioglycolate | — | — |
|  | Cysteamine hydrochloride | 2.7 | 2.7 |
|  | L-cysteine hydrochloride | — | — |
|  | Anhydrous sodium sulfite | — | — |
| Chelating agent | Pentasodium diethylenetriamine pentaacetate | 1 | 1 |
| Alkali agent | Ammonium hydrogen carbonate | 0.4 | 0.4 |
|  | Diammonium dithiodiglycolate | 2.9 | 2.9 |
| Evaluation 2 | Softness | ○ | Reference |
|  | Smoothness | — | Reference |
|  | Moisturizing feeling | ○ | Reference |

Unit of amount of incorporation: mass %

In Table 2 described above, which is related to first agents including cysteamine hydrochloride, it was confirmed that satisfactory feelings of softness and a moisturizing feeling were obtainable as a result of incorporation of N-acetylglucosamine and trehalose.

TABLE 3

|  |  | Example 3 | Comparative Example 3 |
|---|---|---|---|
|  | Common component | 65 | 65 |
|  | N-acetylglucosamine | 0.1 | — |
|  | Trehalose | 0.9 | — |
| Reducing agent | Ammonium thioglycolate | — | — |
|  | Cysteamine hydrochloride | — | — |
|  | L-cysteine hydrochloride | 6 | 6 |
|  | Anhydrous sodium sulfite | — | — |
| Chelating agent | Pentasodium diethylenetriamine pentaacetate | 1 | 1 |
| Alkali agent | Ammonium hydrogen carbonate | 0.4 | 0.4 |
|  | Diammonium dithiodiglycolate | 2.9 | 2.9 |
| Evaluation 2 | Softness | ○ | Reference |
|  | Smoothness | ○ | Reference |
|  | Moisturizing feeling | ○ | Reference |

Unit of amount of incorporation: mass %

In Table 3 described above, which is related to first agents including L-cysteine hydrochloride, it was confirmed that satisfactory feelings of softness, smoothness and a moisturizing feeling were obtainable as a result of incorporation of N-acetylglucosamine and trehalose.

TABLE 4

|  |  | Example 4 | Comparative Example 4 |
|---|---|---|---|
|  | Common component | 65 | 65 |
|  | N-acetylglucosamine | 0.1 | — |
|  | Trehalose | 0.9 | — |
| Reducing agent | Ammonium thioglycolate | — | — |
|  | Cysteamine hydrochloride | — | — |
|  | L-cysteine hydrochloride | — | — |
|  | Anhydrous sodium sulfite | 4.2 | 4.2 |
| Chelating agent | Pentasodium diethylenetriamine pentaacetate | 1 | 1 |
| Alkali agent | Ammonium hydrogen carbonate | 0.4 | 0.4 |
|  | Diammonium dithiodiglycolate | 2.9 | 2.9 |
| Evaluation 2 | Softness | ○ | Reference |
|  | Smoothness | ○ | Reference |
|  | Moisturizing feeling | ○ | Reference |

Unit of amount of incorporation: mass %

In Table 4 described above, which is related to first agents including anhydrous sodium sulfite, it was confirmed that satisfactory feelings of softness, smoothness and a moisturizing feeling were obtainable as a result of incorporation of N-acetylglucosamine and trehalose.

What is claimed is:

1. An agent for hair modification, to be applied on hair in a reduction step for a hair modification treatment method including the reduction step, and a heating step of bringing the hair treated in the reduction step into contact with a heating element, the agent comprising:
    N-acetylglucosamine,
    trehalose,
    ammonium thioglycolate or thioglycolic acid monoethanolamine,
    pentasodium diethylenetriamine pentaacetate,
    ammonium hydrogen carbonate, and
    diammonium dithiodiglycolate,
    wherein the pH of the agent is from 8.0 to 10.0 at 25° C.,
    the viscosity of the agent is from 2,000 to 30,000 mPa·s at 25° C., and
    the agent for hair modification is adapted for being in contact with the heating element set at a temperature of 70° C. or higher.

2. The agent for hair modification of claim 1, wherein the set temperature of the heating element is 80° C. to 230° C.

3. A hair modification treatment method comprising:
    providing a first agent for hair modification that is the agent for hair modification according to claim 1;
    applying the first agent for hair modification on hair; and
    bringing the hair, on which the first agent has been applied, into contact with a heating element set at a temperature of 70° C. or higher.

4. The hair modification treatment method of claim 3, wherein the set temperature of the heating element is 80'C or higher and 230° C. or lower.

5. The hair modification treatment method of claim 3, further comprising applying a second agent comprising an oxidizing agent to the hair after the hair has been brought into contact with the heating element.

\* \* \* \* \*